United States Patent [19]

Shaw et al.

[11] Patent Number: 4,907,795
[45] Date of Patent: Mar. 13, 1990

[54] COMPUTERIZED EXERCISE MONITORING SYSTEM AND METHOD FOR MONITORING A USER'S EXERCISE PERFORMANCE

[75] Inventors: Bon F. Shaw, Winter Park, Fla.; Gary M. Bond, Orlando, both of Fla.

[73] Assignee: Fike Corporation, Blue Springs, Miss.

[21] Appl. No.: 305,545

[22] Filed: Feb. 3, 1989

Related U.S. Application Data

[63] Continuation of Ser. No. 848,215, Apr. 4, 1986, Pat. No. 4,817,940.

[51] Int. Cl.⁴ .............................................. A63B 21/24
[52] U.S. Cl. ..................................... 272/93; 272/118; 272/129; 272/134; 272/DIG. 6
[58] Field of Search ................. 272/93, 117, 118, 125, 272/129-134, DIG. 6; 273/1 GC, 1 GE, 1 GZ; 128/25 R

[56] References Cited

U.S. PATENT DOCUMENTS

| | | | |
|---|---|---|---|
| 4,235,437 | 11/1980 | Ruis et al. | 272/130 X |
| 4,354,676 | 10/1982 | Ariel | 272/129 |
| 4,534,557 | 8/1985 | Bigelow et al. | 272/1 GE X |
| 4,571,682 | 2/1986 | Silverman et al. | 272/129 X |
| 4,601,468 | 7/1986 | Bond et al. | 272/130 |

FOREIGN PATENT DOCUMENTS

| | | | |
|---|---|---|---|
| 0028209 | 5/1981 | European Pat. Off. | 128/707 |
| 0152713 | 8/1985 | European Pat. Off. | 272/93 |

Primary Examiner—Richard J. Apley
Assistant Examiner—Joe H. Cheng
Attorney, Agent, or Firm—Hovey, Williams Timmons & Collins

[57] ABSTRACT

An exercise monitoring system and method for comparing the present movement of the exercise machine caused by the physical exertion of a user with the user's past movement of the exercise machine. The system includes an exercise monitoring main unit, an exercise monitoring screen, a portable personal memory module, an exercise machine monitoring device, and an exercise monitoring analyzer. The exercise machine monitoring device measures the movement of the exercise machine and provides data representative thereof. The portable personal memory provides data representative of the user's past movement of the exercise machine. The exercise monitoring main unit compares the data and generates a pacing signal on the exercise monitoring screen for the user. The user follows the pacing signal to duplicate his previous performance. The exercise monitoring screen discipline the user's present pace compared to his past pace. The display includes a row of red, yellow and green lights which indicate whether the user is exercising too slowly or too fast. The user can optionally update the portable personal memory with his present performance. The portable personal memory can be transported to provide training on various exercise machines.

8 Claims, 11 Drawing Sheets

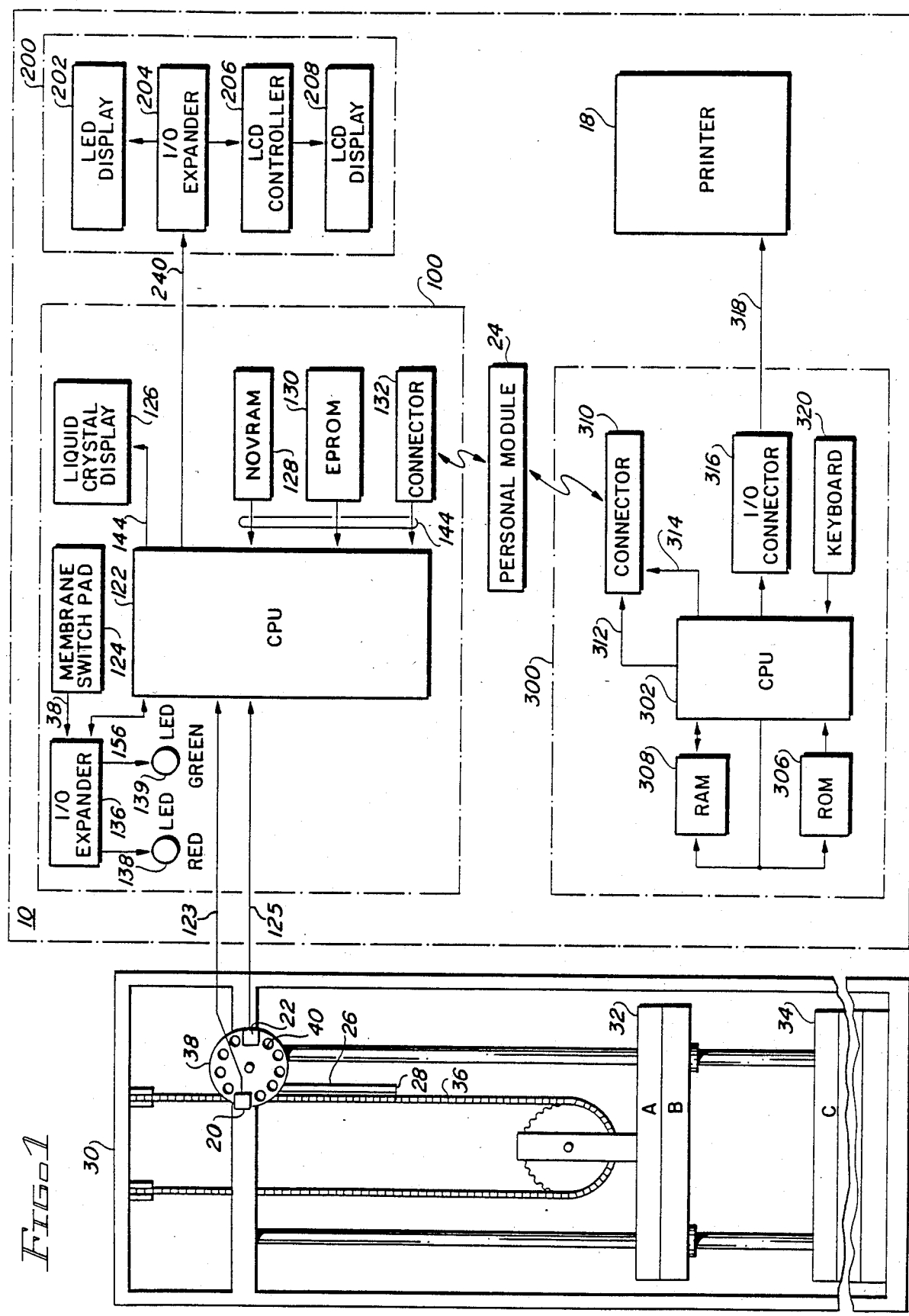

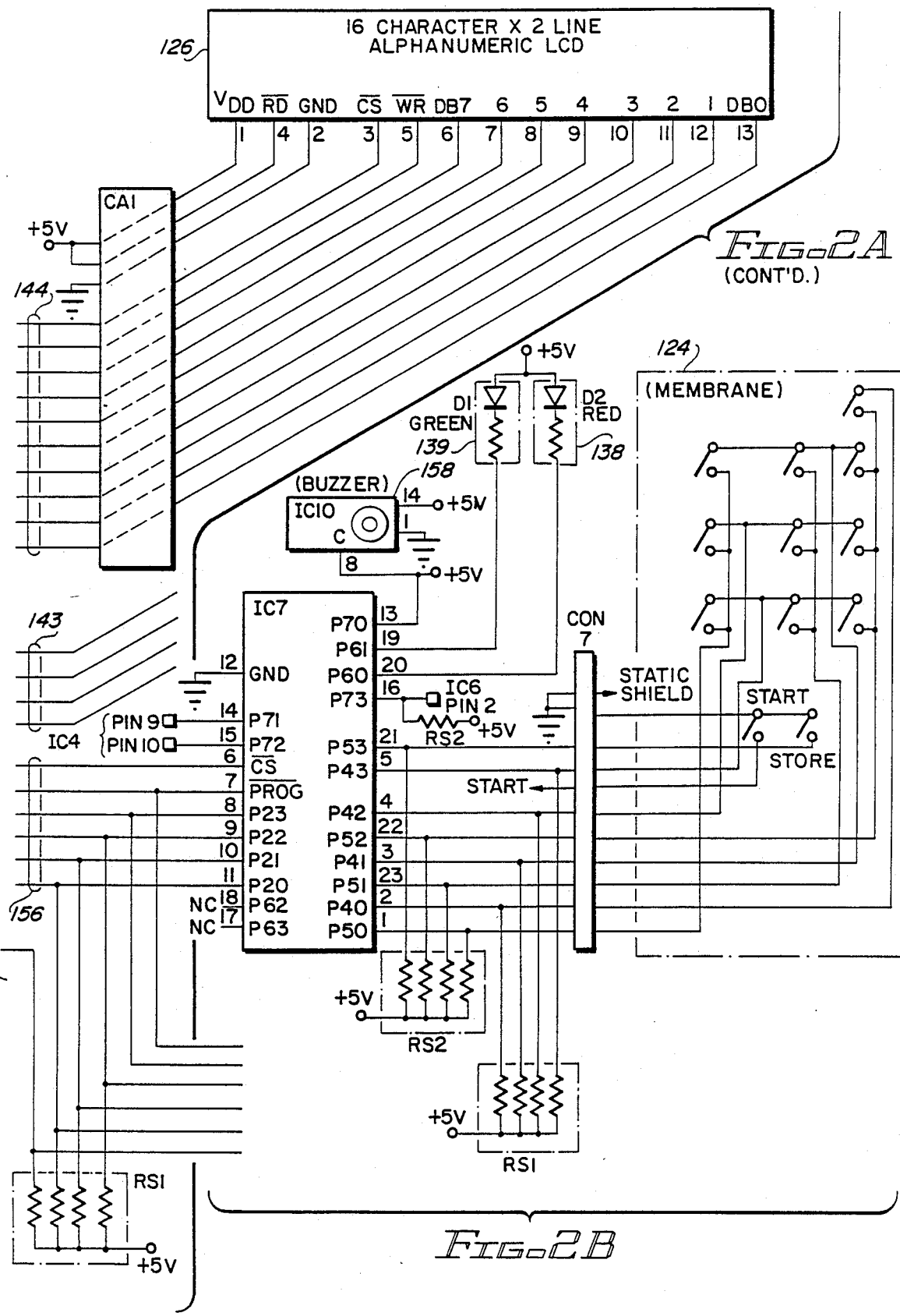

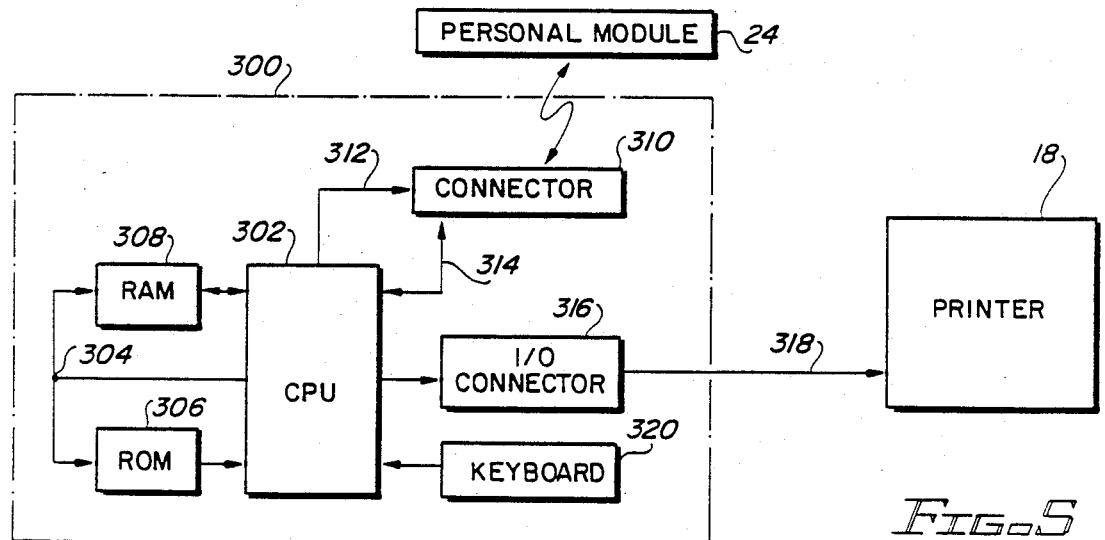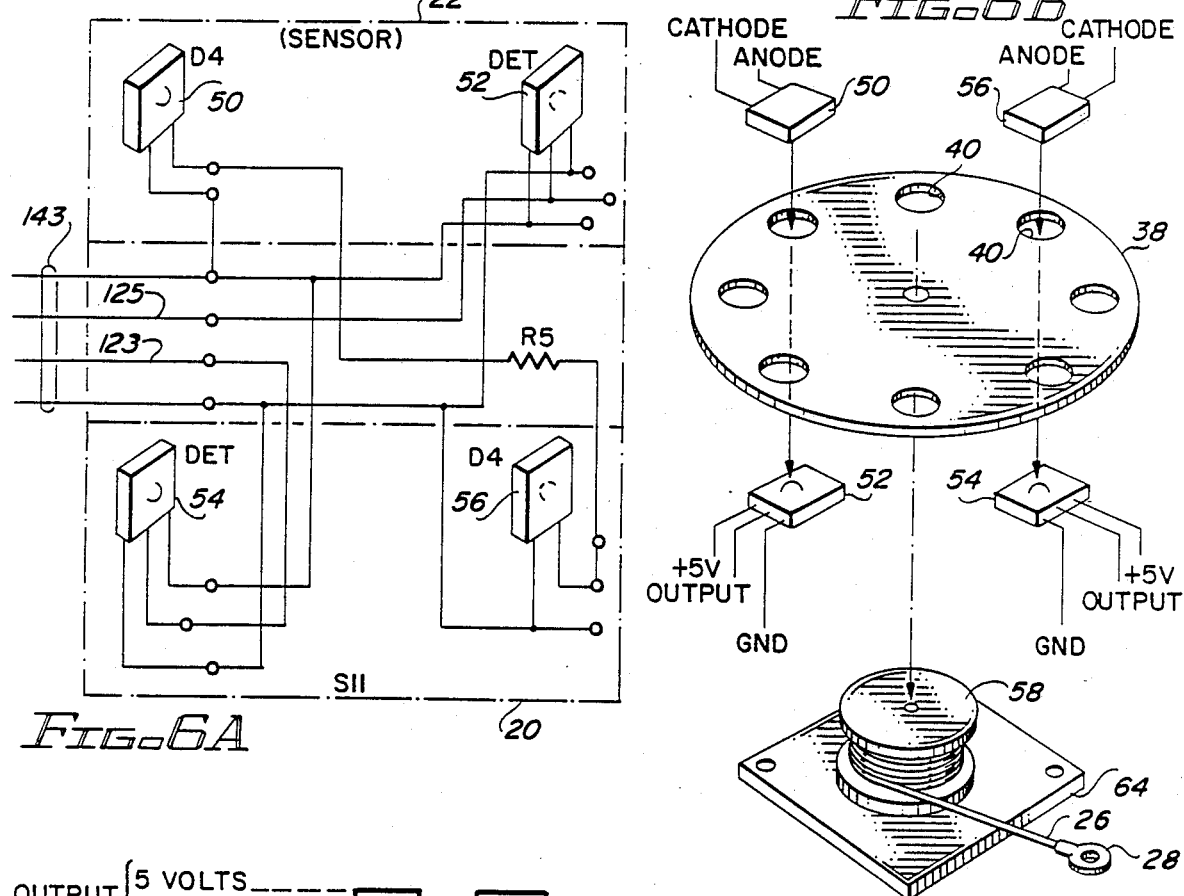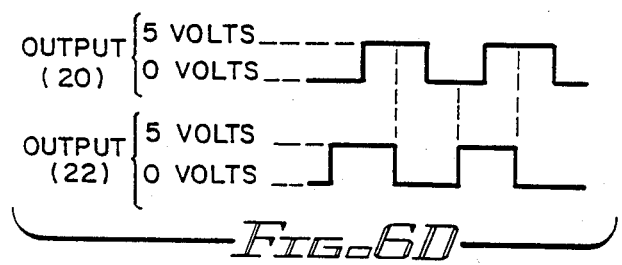

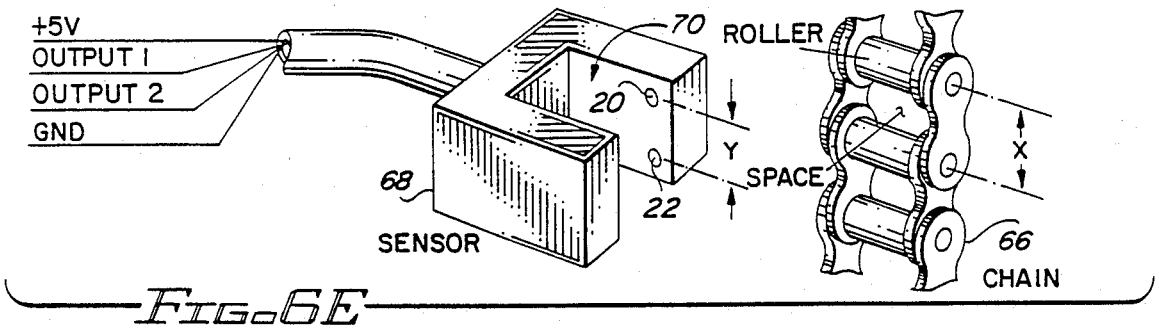
FIG. 6E
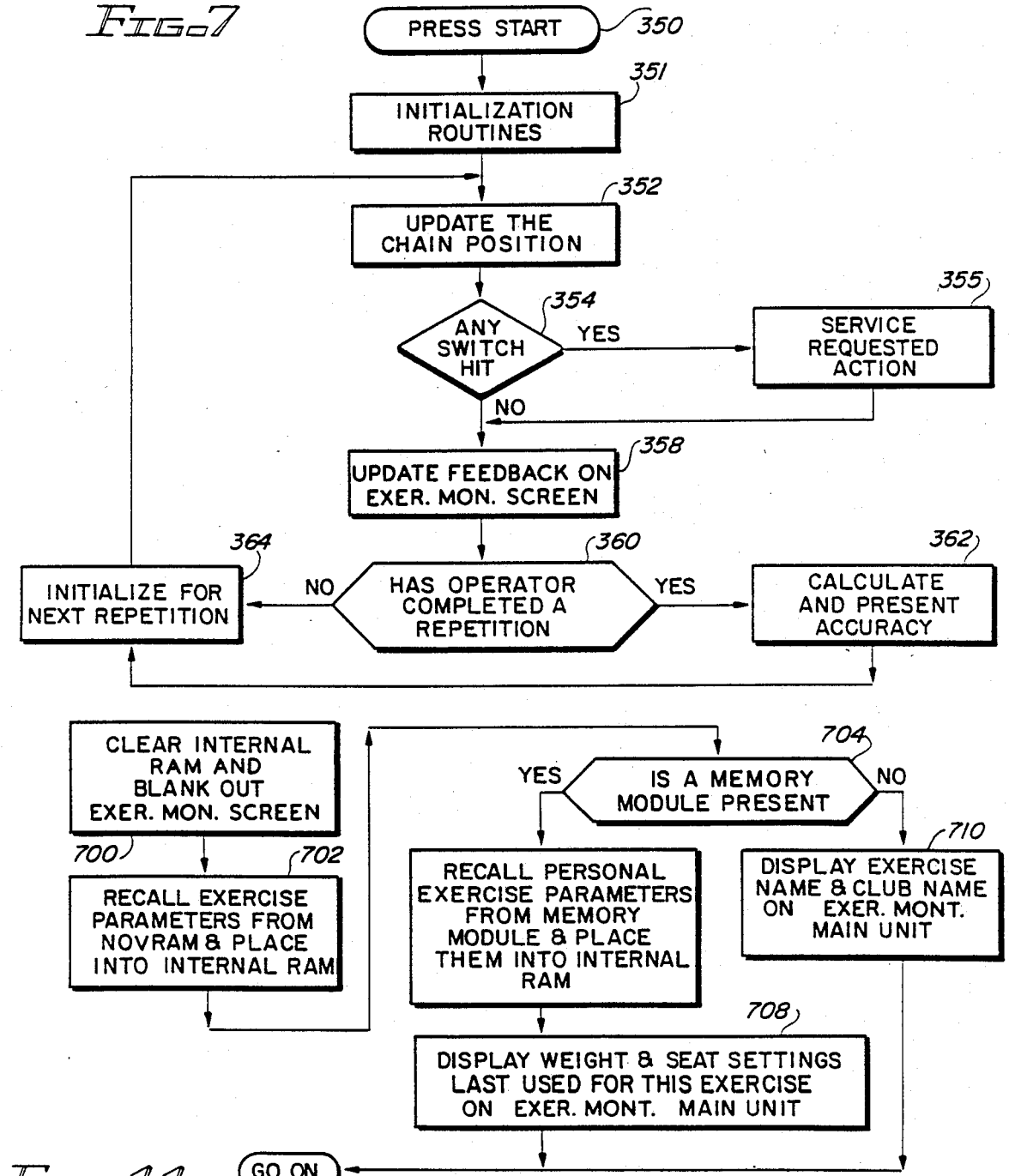
FIG. 7
FIG. 11

COMPUTERIZED EXERCISE MONITORING SYSTEM AND METHOD FOR MONITORING A USER'S EXERCISE PERFORMANCE

This is a continuation of application Ser. No. 06/848,215, filed on A.il 4, 1986, now U.S. Pat. No. 4,817,940.

FIELD OF THE INVENTION

The invention relates to a computerized exercise monitoring system, and a method for using the system on exercise equipment to provide performance information.

BACKGROUND OF THE INVENTION

Routine physical exercise has long been extolled by medical authorities as essential to good health and longevity. There have been devices which tell a person exercising on an exercising apparatus the amount of exercise accomplished by that person. Examples of these are U.S. Pat. Nos. 4,493,485, 4,409,992 and 4,408,183. However, these devices have been limited to monitoring current use of the exercise machine. These devices gave no indication of the amount of present exercise activity as compared to the amount of previous exercise activity accomplished by the user of the equipment. For example, in U.S. Pat. No. 4,493,485 the device provides a standard predetermined pace for the person to follow. The pace is based on a precalculated exercising profile of another, not on the user's past exercising efforts.

It is important that a person using exercise equipment be aware of how much exercise he has accomplished, and of any increase in the amount of exercise performed over time. It will be helpful if a record can be made of the user's performance, and later used to compare the present exercise routine with previous routines to measure the user's progress. The present invention encourages the user to perform a more efficient workout by comparing each exercise repetition of the exercise machine with the user's previous best efforts, or with a coach's performance.

A problem with previous computerized exercise monitoring equipment was the inability to exercise on various exercise equipment. In previous systems, the user was forced to continuously use the same machine. It would be desirable if a record of the user's performance is stored on a portable memory unit. The portable memory unit would be inserted into the exercise monitoring unit for each exercise machine. The portable memory unit (personal module) would contain data of a user's previous efforts on the exercise machine. The data on the personal module would be read by the exercise monitoring unit and would compare the present workout with the user's previous workout while the user is exercising. The personal module would also store information about previous workouts such as date of workout, weight use, exercise repetitions completed, and average accuracy of the repetitions. The system would provide a person with the ability of comparing his workouts with previous workouts. The user would progress in his workout compared to his own ability, rather than compared to another's workout. The present invention provides such a system.

Another advantage of this system is its adaptability to various types of exercise machines. Each exercise machine has an exercise monitoring main unit and an exercise monitoring screen attached to it. The exercise monitoring screen constantly displays the user's performance data and a count of the completed repetitions. The exercise monitoring main unit computes the users previous pace and monitors his present pace compared to the previous pace on a display. The display shows graphically whether the exercise user is performing the exercise for maximum physical performance, based upon the user's previous performance.

Accordingly, it is an object of the present invention to provide an exercise system and method for providing a progressive exercise routine for a person based on his own ability.

It is another object of the present invention to provide a system and a method for providing progressive training on various exercise machines.

It a further object of the present invention to provide a more efficient workout to the user by comparing each exercise repetition with the user's previous best effort, or with his past performance.

It is yet another object of the present invention to provide a pacing signal for the user based on his own ability.

It is still a further object of the present invention to store the user's past performances on a portable exercise monitoring personal module, so that the user can recall past performances on the exercising machine.

It is a further object of the present invention to display data regarding the user's previous performance so it may be compared to present performance.

It is a further object to provide an exercise monitoring analyzer to report to the user progress on his present workout performance.

It is a further object of the present invention to provide a user with a portable exercise monitoring personal module which contains the user's previous efforts.

A further object of the present invention is to provide to the user with an indication of how to change his rate of exercising to obtain the maximum benefit from the exercise routine.

Another object of the present invention is to compute the primary faults of the user during his exercise routine and display them in an easily readable form.

SUMMARY OF THE INVENTION

The exercise monitoring system monitors electrical signals representative of the movement of an exercise machine caused by a physical exertion of a user. The movement corresponds to the user's exercise performance. The exercise monitoring system compares the prevent movement of the exercise machine with criteria representative of the user's previous exercise performance. A display of the exercise monitoring system indicates to the user his present exercise performance compared to his previous exercise performance. The exercise monitoring system has the option of storing the user's present performance for use as a past performance.

The exercise monitoring system comprises a monitoring means for measuring the movement of the exercise machine which corresponds to a user's exercise activity and provides signals representative of this activity. A memory means provides signals representative of the user's previous exercise activity. An evaluating means coupled to the monitoring means and memory means receives the signals representative of the user's present exercise activity and the past signals representative of the user's previous exercise activity. The evaluating means compares the two signals and produces a pacing signal. The pacing signal causes a plurality of light emitting diodes to produce a display for the user. The user follows the display to reproduce his previous workout.

In the illustrated embodiment, the exercise monitoring system is a computerized exercise monitoring system and method to be used in conjunction with other exercise equipment. The system encourages the user to perform a more efficient workout by comparing each exercise repetition with the user's best effort, or with a coach's performance. All workout routines are stored by the system in an exercise monitoring personal module, so that graphs, charts and analyses can be printed on a print-out or plotted on a graph showing a user's progress.

The exercise monitoring system includes five components: an exercise monitoring main unit; an exercise monitoring screen; a portable exercise monitoring personal module; an exercise machine sensor and an exercise monitoring analyzer. It is desirable that one exercise monitoring main unit and one exercise monitoring screen are used in conjunction with an exercise machine. The exercise monitoring main unit contains a microcomputer to monitor the user's performance. The user of the machine has a portable exercise monitoring personal module, about the size of a cigarette package, which is inserted into the exercise monitoring main unit before the user begins his exercise routine. The exercise monitoring personal module contains information about the user's previous workouts on the particular exercise machine, as well as certain personal characteristics of the user, including weight, beginning date of workout, number of workouts, and number of repetitions.

After the exercise monitoring personal module is inserted, the exercise monitoring main unit displays the user's weight, seat settings for the exercise machine, and the user's past performances on the machine, including the dates of previous workouts, weight use, repetitions completed and average accuracy of the repetitions.

While exercising on the machine, the user watches the exercise monitoring screen so that he may compare each current repetition with his previous effort. The exercise monitoring screen is a display screen mounted in a position for easy viewing by the user while exercising. The exercise monitoring screen comprises a row of red, yellow and green lights which indicate whether the user is exercising too slowly, or too fast, compared to his previous rate. A separate red light turns on when the user rests between repetitions to discourage resting. A separate green light turns on at the height of each repetition to encourage the user to pause momentarily to gain maximum benefit from the workout. After each repetition, the exercise monitoring screen displays an accuracy number computed by the exercise monitoring main unit which represents how closely the current repetition matches the user's personal best effort. Also displayed is the number of completed repetitions.

If a user exercises on a exercise machine equipped with a exercise monitoring main unit and exercise monitoring screen, but does not use an exercise monitoring personal module, the exercise monitoring main unit computes the user's performance as compared with the performance of a coach or other person whose data are stored in the exercise monitoring main unit memory. The exercise monitoring main unit computes the user's performance and displays the information on the exercise monitoring screen, just as if the exercise monitoring personal module were in use.

A workout record is the information gathered by the exercise monitoring main unit during a user's workout on a particular exercise machine. The workout records are stored in the user's exercise monitoring personal module. The exercise monitoring analyzer converts the exercise information from the workout record into printed plots and graphs to provide a visual progress guide. The printout provided by the exercise monitoring analyzer identifies the particular exercise machine, the date of the workout, the number of repetitions completed, the weight used and the average of the accuracy numbers received for a set of repetitions. The exercise monitoring analyzer also computes the user's primary faults, such as exercising too fast or too slowly, resting between repetitions, or failing to pause at the height of each repetition.

The exercise monitoring system also includes a universal exercise monitoring sensor, which senses the motion of the exercise machine. The sensor is comprised of a plastic or metal disc attached to a base mounted reel with a built in steel spring. The disc has a series of equally spaced holes on its circumference. A steel cable with a metal ring on one end is wrapped around the reel and securely fastened. The metal ring is connected to the weight stack or the moving part of the exercise machine. As a steel cable is pulled off the reel, the disc rotates with the holes interrupting the infrared beams from the output of two infrared detectors situated on each side of the disc. The infrared detectors are spaced at a distance so as to create two square waveforms approximately ninety degrees out of phase when the disc is rotated. As the user pushes against the weight stack or other moving part of the exercise machine, the steel cable attached to the moving part rotates the reel and the disc attached to the reel. The exercise monitor monitors the output from these sensors to show the position of the moving weight stack.

Also, the infrared detectors can be situated on each side of a chain. As the chain is moved, it creates two square waveforms approximately 90° out of phase, which can be measured by the exercise monitoring unit. In this manner, the exercise monitoring unit measures the movement of the weight stack resulting from the user's exercise on the machine.

BRIEF DESCRIPTION OF THE DRAWINGS

Those and other objects and advantages of the present invention will become more apparent by referring to the following detailed description and accompanying drawings in which:

FIG. 1 shows a basic diagram of the components of the exercise monitoring system;

FIGS. 2A-B show a detailed circuit diagram of the exercise monitoring main unit;

FIG. 5 shows a block diagram of the exercise monitoring analyzer;

FIG. 6A-E show a detailed diagram of the elements of the exercise monitoring sensor;

FIG. 7 illustrates the overall monitoring routine of the exercise monitoring main unit.

FIG. 11 shows a flow diagram for the initialize routine for the exercise monitoring main unit.

DESCRIPTION OF AN ILLUSTRATIVE EMBODIMENT

Figure 2A:
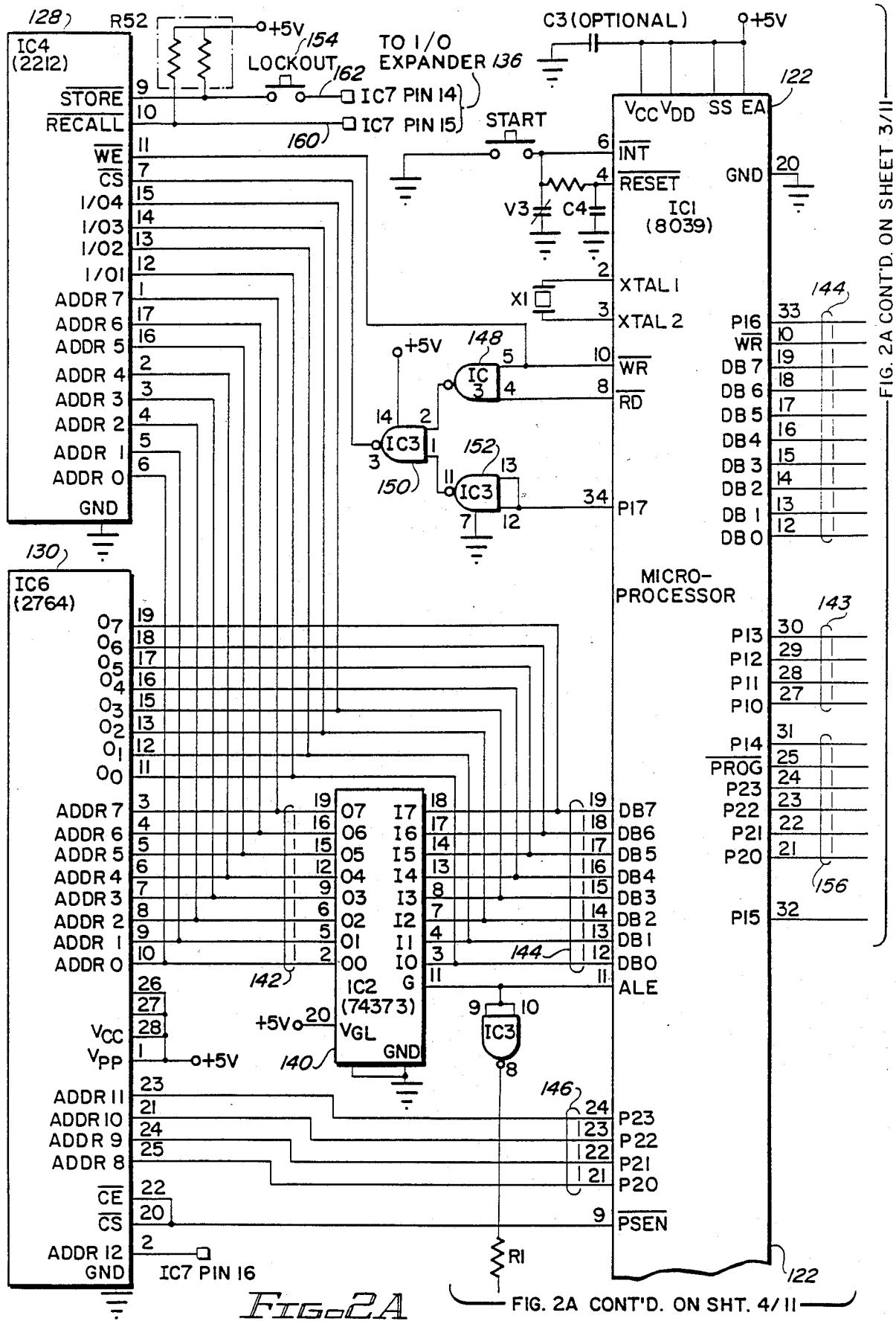

A. General Description of the Exercise Monitoring System

Referring now to the drawings, FIG. 1 shows an exercise monitoring system 10 adapted for coupling by sensors 20 and 22 to an exercise machine 30 to receive on lines 123 and 125 signals to be processed and stored in an electrically erasable programmable read only memory EEPROM 44 of the exercise monitoring system 10. The exercise monitoring system 10 is capable of monitoring the movements of any exercise machine that has a moving part, such as a chain. The exercise monitoring system 10 is comprised of the exercise monitoring main unit 100, the exercise monitoring screen 200, the exercise monitoring analyzer 300, an exercise monitoring personal module 24 and a printer/plotter 18.

1. Exercise Monitoring Main Unit

The exercise monitoring unit 100 monitors the movements of the exercise machine 30 via lines 123 and 125, connected to sensors 20 and 22, respectively, Sensors 20 and 22 produce an output based upon the displacement of weights 32 of the exercise machine 30. The exercise machine consists of chains and gears, so that during use, when a handle or bar is displaced, a corresponding amount of displacement is made in the weights 32. The weights 32 can be increased by the addition of other weights 34.

In most typical exercise machines, the weights are labeled so that the lightest weight is A, the next weight added is B, and so on. Thus, the amount of weight used on each exercising machine is known by referring to the letter of the weight used. For example, if four weights are used, the letter D would correspond to four weights on the weight stack.

The sensors 20 and 22 each consist of an infrared emitter and an infrared detector. The infrared emitter emits infrared light which is detected by the infrared detector. The infrared detector outputs a signal, depending upon the amount of infrared light in impinging upon it. This signal is a TTL compatible signal fed to the exercise monitoring main unit 100. When the user begins a repetition, the cable 26 connected to a metal ring 28 is attached to the chain 36 of the exercising machine 30. When the user starts the repetition, the force applied to a bar or handle is translated to movement in the chain 36. This movement is transferred to the cable 26, which causes disc 38 with holes 40 in it to rotate. The rotation of the disc causes a pulse signal from the detector of sensors 20 and 22 to be sent to the exercise monitoring main unit 100. From these pulse signals, the exercise monitoring main unit computes the movement of the weights and the rate of movement of the weights. For a better understanding of the configuration and functional cooperation of the components described briefly above, attention is directed to FIG. 6 of the drawings wherein the respective components of the sensors are illustrated in detail.

The exercise monitoring main unit 100 is comprised of a microcomputer 122, a membrane switch pad 124, a liquid crystal display 126, a nonvolatile random access memory (NOVRAM) 128, a programmable read only memory PROM 130, a personal module connector 132, an I/O expander 136, a red LED 138 and a green LED 139. The microcomputer 122 receives the TTL level signal output from the sensors 20 and 22 through lines 123 and 125. The microcomputer 122 executes the exercise monitoring main unit software contained in PROM 130. It is understood that microcomputer 122 has its own internal clock, as is well known in the art, for controlling its internal operation as well as its interfacing with other elements of the exercise monitoring system 10.

The microcomputer 122 also has an internal RAM contained in the microcomputer 122 itself. The internal RAM of the microcomputer 122 is downloaded and uploaded from the NOVRAM 128. The microcomputer 122 is coupled by a control bus 127 and data bus 144 to each of the PROM 130 and to the NOVRAM 128. The PROM 130 is adapted to store the instructions which the microcomputer 122 executes to detect and recognize the input sensor signals, to process these signals, and to store the processed signals in designated areas of the NOVRAM 128. The programs or routines stored in the PROM 130 are explained generally with respect to FIG, 7 through FIG. 9.

The microcomputer 122 also outputs to the liquid crystal display 126 through bus 142. The liquid crystal display provides the user with an indication of the particular mode of operation of the microcomputer 122. The mode of operation of microcomputer 122 can be changed via operator input through the membrane switch pad 124. The membrane switch pad 124 is connected through connector CON 7 to an I/O expander 136, and to the microcomputer 122 via bus 156. The microcomputer 122 also controls the illumination of LED 138 and LED 139 through bus 134 and I/O expander 136. If the exercise monitoring personal module 24 is not physically connected to connector 132 the microcomputer 122 illuminates the red LED 138. This notifies the user, that the exercise monitoring personal module 24 is not present, or that the physical insertion of the exercise monitoring personal module 24 into the exercise monitoring main unit 20 is faulty. When the exercise monitoring personal module 24 is physically connected to the connector 132, the microcomputer 122 senses the connection and illuminates the green LED 139 to signify to the user that the exercise monitoring personal module 24 is properly connected. The connector 132 is connected to the data bus 144 of the microcomputer 122 in a manner well known in the art. The control bus 144 is also connected to the connector 132, so that when the exercise monitoring personal module 24 is connected to the connector 132, the microcomputer 122 can input and output data to the exercise monitoring personal module 24.

The exercise monitoring personal module 24 contains an electrically erasable programmable read only memory EEPROM 44 to receive and store personal data of the user. Each user of the exercise machine 30 has an exercise monitoring personal module 24. The exercise monitoring personal module 24 contains the data necessary for the microcomputer 122 to compute the performance characteristics of the user for the particular exercise machine 30. Because of the universal nature of the exercise monitoring unit 100 and the sensors 20 and 22, the exercise monitoring main unit 100 can be connected to any exercise machine. It is important to note that the exercise monitoring personal module 24 contains user data for every exercise machine available. The personal module may be removed from the exercise monitoring main unit 100 connected to a particular exercise machine, and inserted into another exercise monitoring main unit connected to a different exercise machine. The exercise monitoring main unit software from operator input determines the correct performance data for the user on the particular exercising machine.

If the user's current repetition is nearly identical to the user's best effort, the exercise monitoring screen displays an accuracy number of 99, which means the user is within 99 percent of duplicating his previous personal best effort. The exercise monitoring main unit computes an accuracy number which reflects when a user exercises too fast or too slow, rests between repetitions, or fails to pause at the height of the repetition. The greater the faults, the lower the accuracy number. The repetition count advances only if the exercise monitoring main unit determines that the weight has traveled to within 87.5% of the distance recorded in the user's previous effort.

2. Exercise Monitoring Personal Module

The heart of the system is the exercise monitoring personal module 24. The exercise monitoring personal module 24 contains data for the user of the personal module. The data contains the best effort or past performance of the user for each exercise machine he has previously used. When a user inserts the exercise monitoring personal module 24 into the exercise monitoring main unit connector 132, the microcomputer 122 reads the user's personal database stored on the personal module 24 for the particular exercise machine, and displays the user's weight settings and seat settings for the particular exercise machine. Through the switch pad 124, the user requests a display of his past performances on the particular exercising machine, including the dates of his workouts, weight used, repetitions completed and average accuracy of the repetitions. The user can also store a particular exercising routine performed on the exercise machine in the exercise monitoring personal module 24. In this manner, a user continuously updates the exercise monitoring personal module 24 with his best or past performance.

The personal module 24 is then physically removed from the exercise monitoring main unit 100 upon completion of the particular exercising routine for this exercise machine. The user then carries the personal module 24 to another exercise machine and insert his personal module 24 into the exercise monitoring main unit connected to that exercise machine. The personal database for the user on this machine is also stored on the personal module 24. When the user completes an exercising routine on the machine, he then continues to the next machine. Upon completing a set of exercise routines on several different exercise machines, the user then carries his personal module 24 to the exercise monitoring analyzer unit 300 for analysis.

3. Exercise Monitoring Screen

The microcomputer 122 of the exercise monitoring main unit 100 is connected to the exercise monitoring screen 200 by bus 140. The exercise monitoring screen 200 includes an LED display 202, an I/O expander 204, an liquid crystal display controller 206, and an LCD display 206. The I/O expander 204 of the exercise monitoring screen 200 is one typically used in interfacing microcomputers, and is known to those of ordinary skill in the art. The microcomputer 122 addresses the LED display 202 and LCD display 208 through the I/O expander 204. The I/O expander 204 is directly connected to the LED display 202. The LED display includes a row of red, yellow and green lights. The I/O expander 204 is also connected to an LCD controller 206 which energizes the LCD display 208. The LCD display 208 displays the repetition and accuracy numbers representative of the exercising performance of the user. The exercise monitoring main unit 100 calculates performance factors of the repetitions of the user. The performance factors include the rate of exercising and the number of repetitions. The rate of exercising is calculated in the microcomputer 122 and transferred to the LED display 202 of the exercise monitoring screen 200. The LED display 202 includes a row of red, yellow and green LEDs to indicate whether the exercise rate of the user is too slow, too fast or equal to the best or past performance as read from the user's exercise monitoring personal module 24. In addition to the row of red, yellow and green LEDs, there is a red LED to discourage resting, which is illuminated by the software of microcomputer 122, and a green LED which turns on at the height of each repetition to encourage the user to pause momentarily. The performance of the user is recorded in the microcomputer 122 and used to calculate the accuracy number.

The accuracy number represents how closely the present repetition of the user matches a previously stored repetition on the exercise monitoring personal module 24. If the repetition is nearly identical to the user's best efforts, the exercise monitoring screen displays an accuracy number of 99, which means the user is within 99 percent of duplicating his previous personal best effort. The exercise monitoring main unit computes an accuracy number, which is lower when a user exercises too fast or too slow, rests between repetitions, or fails to pause at the height of the repetition. The repetition count advances only if the exercise monitoring main unit determines that the weight has traveled to within 87.5% of the distance recorded in the user's previous efforts.

4. Exercise Monitoring Analyzer

The exercise monitoring analyzer 300 is comprised of a microcomputer 302, ROM (306), RAM (308), connector 310, I/O connector 316, and keyboard 320. The microcomputer 302 has its own internal clock, as is well known in the art, to control its internal operation as well as its interfacing with other elements of the unit 10. The microcomputer 302 is coupled with an instruction data (I/D) bus 304 through each of a ROM 306 to the RAM 308. The ROM 306 is adapted to store the instructions which the microcomputer 302 executes, to process the data from the personal module 24, and to analyze this data and output it to the printer/plotter unit 18. The personal module 24 is electrically connected to the microcomputer 302 via connector 310. The microcomputer 302 reads the data in the personal module 24 through control bus 312, and accesses the data in the personal module 24 via data bus 314. The microcomputer 302 analyzes the user's personal data on the personal module 24 and outputs a workout record to the printer/plotter 18 connected to the I/O connector 316 via bus 318. The exercise monitoring analyzer 300 converts the exercise information from the workout records into printed plots and graphs to provide a visual progress guide for the user. The printout provided by the exercise monitoring analyzer 300 identifies each exercise machine, the date of the workout, the number of repetitions completed, the exercising machine weight used, and the average in the accuracy numbers received for a set of repetitions. The exercise monitoring analyzer 300 also analyzes the user's primary faults, such as exercising too fast or too slowly, resting between repetitions or failing to pause at the height of each repetition.

B. Detailed Description of the Exercise Monitoring Main Unit

1. Exercise Monitoring Main Unit

Figure 2A:
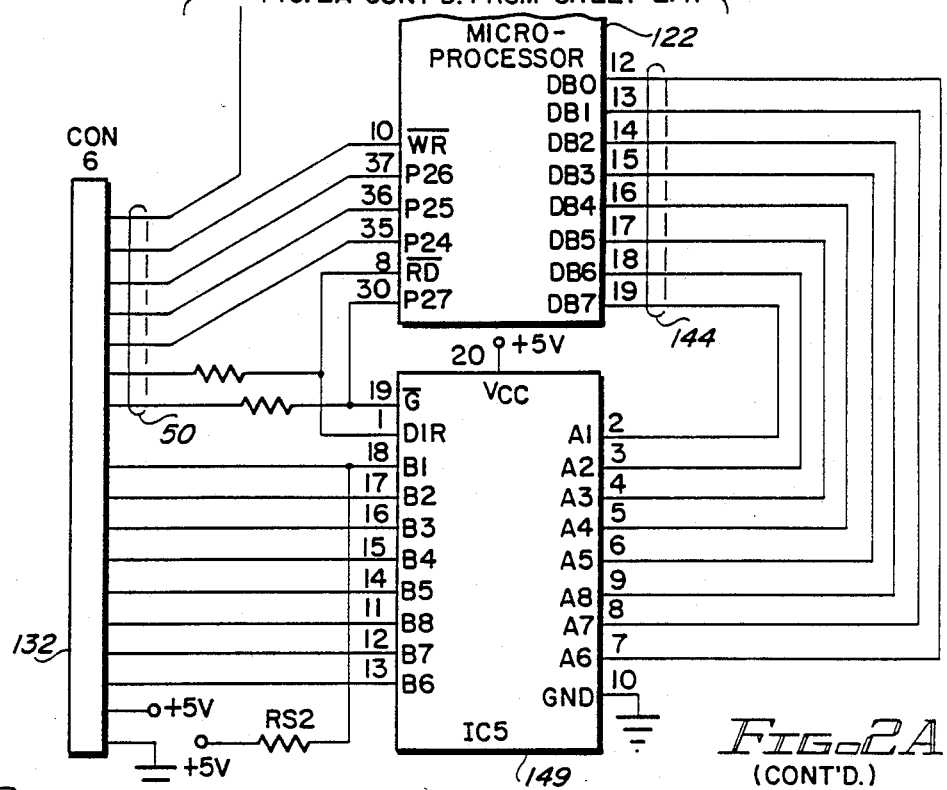

Referring to FIGS. 2A-B there is shown a detailed circuit diagram of the exercise monitoring main unit 100. The microcomputer 122 found principally in FIG. 1 and 2 may illustratively take the form of a microprocessing unit manufactured by INTEL under their designation 8039H. The microcomputer 122 in conjunction with address latch 140 receives and transmits data via its address bus 142, the data bus 144, and high order address lines 146. For clarity in the figures some of the lines and buses are duplicated. The sensors 20 and 22 transfer data to and from the microcomputer 122 via ports P10 through P13 through bus 143. Bus 143 contains the sensor lines 124 and 126. The PROM 130 may take the form of a memory device as manufactured by INTEL under their designation 2764. The data bus 144 connects the data ports DB7–DB0 of the microprocessor 122 to the data ports $0_0$–$0_7$ of PROM 130. The address bus 142 of microprocessor 122 is connected to the low order address ports ADDR0–ADDR7 of the PROM 130. The high order address line 146 of the microprocessor 122 is connected to the high order address ports ADDR8–ADDR11 of the PROM 130. When the EPROM 130 is addressed, instructions of the microprocessor programs are read out via the data ports $0_0$–$0_7$ and transmitted via data bus 144 to the microcomputer 122.

The NOVRAM 128 is comprised of two memory elements, a volatile element and non volatile element, as manufactured by XICOR under their designation X2212. The low order lines of the data bus 144 are connected to the data ports I01 through I04 to the NOVRAM 128. The address bus 142 is connected to the address ports ADDR0–ADDR7 of NOVRAM 128. As shown in FIG. 2A, addresses are applied via the address bus 142 to the elements of the NOVRAM 128 and of the EPROM 130 to address one of the elements and a selected location therein. Microcomputer 122 generates a particular location within one of the elements of the EPROM 130 or the NOVRAM 128 to be addressed. The addresses are selected by an address latch 140, whose inputs are taken from the port ALE and DB0–DB7 of the microcomputer 122. The address latch 140 provides output signals on the address bus 142 to each of the aforementioned elements to address a single location therein. The microcomputer 122 generates a signal on the program store enable PSEN to select the EPROM 130, for program input. To select the NOVRAM 128, the microcomputer activates the RD line, WR line, and port P17. The write line (WR) and the read line (RD) are inputs to a NAND gate 148. The output is activated on both lines going high. The output enables a second NAND gate 150. Port 17 provides an inverted input through inverter 152 to the NAND gate 150. When strobed, the write line, read line, and port 17 select NOVRAM 128 for input and output.

The recall port and store port of the NOVRAM 128 perform a special function for the NOVRAM 128. The NOVRAM 128 comprises two identical memory elements. One memory element is nonvolatile and does not change its state upon a power failure. The other element is volatile and can be changed. When the store function of the NOVRAM is activated, the nonvolatile element is copied to the volatile element. When the store function is activated the volatile element is copied to the nonvolatile element. The operating characteristics of the exercise machine connected to the exercise monitoring main unit is stored in the nonvolatile element of the NOVRAM 128. When a power failure occurs or on power up the nonvolatile memory of NOVRAM 128 is copied to the volatile element of the NOVRAM 128. If the particular operating characteristics of the exercise machine are changed, then the store line is activated. Two criterion accomplish store line activation. First the microcomputer 122 raises the store line, and a lockout switch 154 is simultaneously activated by the user. The lockout switch 154 prevents the configuration stored in the NOVRAM 128 from inadvertent change.

The personal module 24 is connected to the microprocessor 122 by a female connector 132. An address latch 149 is connected between the data bus 144 and the personal module 24. Latch 149 is enabled by the ports RD and P27 of the microprocessor. When the personal module is connected into the female connector 132 the control lines, address lines, and data lines are available for the microcomputer 122 to read or write to the personal module 24, in a manner well known in the art.

The data bus 144 couples a 16 by 2 alphanumeric liquid crystal display 126 to the microprocessor 122. Data from the microcomputer 122 in the form of 32 ASCII characters are output to the liquid crystal display for observation by a user. The ports designated write enable and P16, control the write enable and chip select of the LCD display 126.

Referring to FIG. 2B, there is shown a detail circuit diagram of the I/O Expander 136 and the membrane switchpad 124. The ports designated P20 to P23, P14, and PROG connect the I/O expander 136 to the microcomputer 122 through control bus 156. Port P14 enables I/O expander 136 by being connected to the chip select of I/O expander 136. The I/O expander 136 illustratively takes the form of a I/O expander manufactured by INTEL under their designation 8243. The I/O expander 136 contains four I/O ports designated as P40–P43, P50–P53, P60–P63 and P70–P73 which serve as an extension of the microcomputer 122 I/O bus. All communication between the I/O expander 136 and the microcomputer 122 occurs over P20 to P23. The timing is provided by an output pulse on the program pin (PROG) of the microcomputer 122. Each transfer consists of two four bit nibbles, the first nibble containing the port address and the second nibble containing the four bits of data. The selection of a port and the input/output condition is selected by ports 20 through 23. For example, if port 21 and port 22 are both low then ports 40–43 on I/O expander 136 are selected. If port 23 and port 20 are both low a read instruction is specified. In this manner, the I/O expander 136 can communicate to four bi-directional I/O ports.

The membrane switch pad 124 is connected to ports 40–43 and ports 50–53 on the I/O expander 136. The red LED 138 is connected through the I/O expander 136 through port 60 and the green LED 139 is connected to port 61. The green LED 139 signifies that the personal module 24 is inserted into the microcomputer 122. The red LED signifies the personal module 24 is not connected.

A buzzer 158 is connected to the I/O expander 136 via port 70. The user inputs through the membrane switchpad 124 to the microprocessor 122. When the user activates a certain switchpad, the microcomputer 122 reads the input from the I/O expander 136. The microcomputer 122 corresponds to the input by activating the buzzer 158. The recall line and store line of the NOVRAM 128 are connected respectively to the I/O expander's port 72 and port 71. The activation of the recall line 160 copies the NOVRAM's 128 nonvolatile memory to the volatile memory. The store line 162 and the lockout switch 154 when activated, copies volatile memory to the nonvolatile memory element.

2. The Exercise Monitoring Personal Module.

Figure 3:
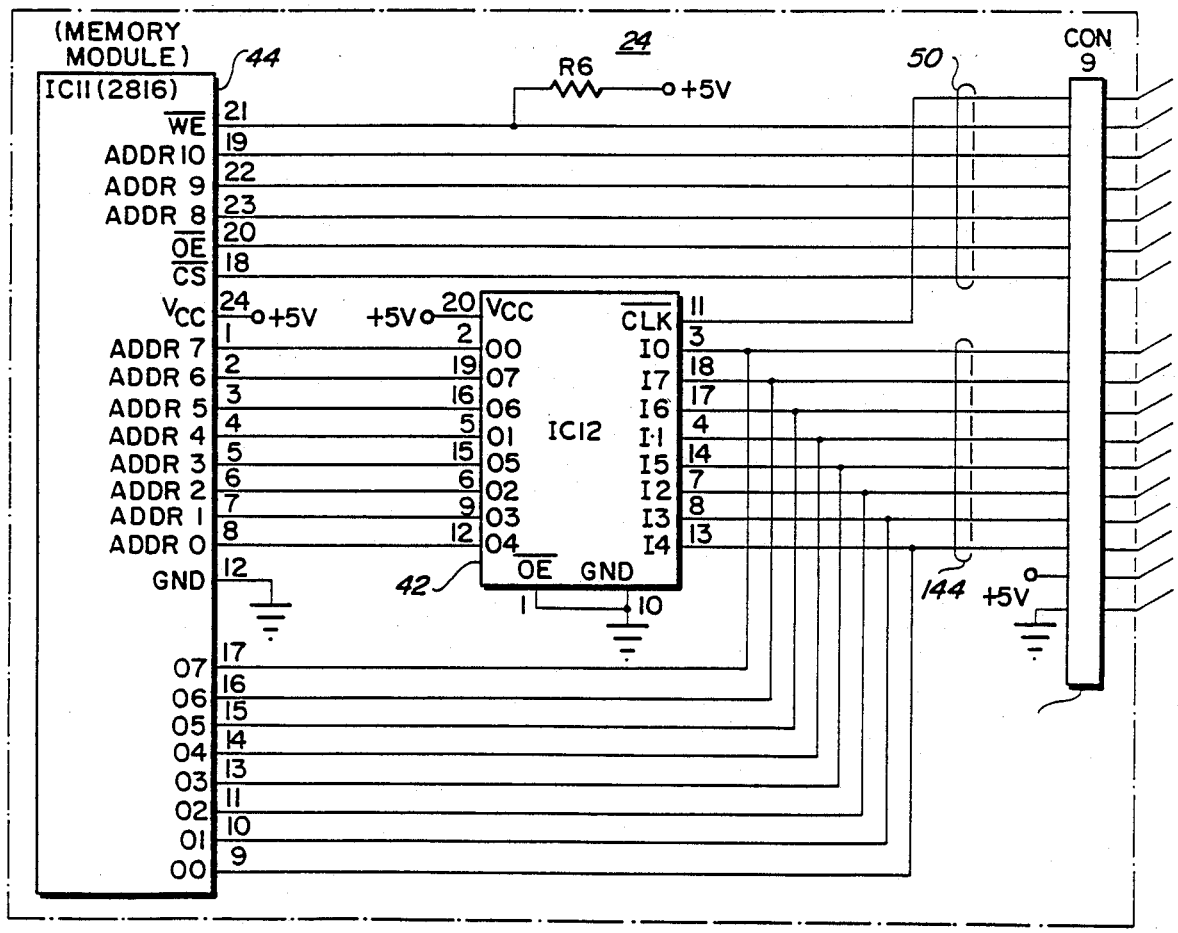
FIG. 3 shows a detailed circuit diagram of the exercise monitoring personal module.

Referring to FIG. 3 there is shown a detailed electrical diagram of the exercise monitoring personal module 24. The personal module 24 comprises a connector CON 9, an address latch 42, and an electrically erasable programmable read only memory EEPROM 44. The EEPROM may illustratively take the form of a memory element manufactured by XICOR under their designation 2816. The connector 40 allows a personal module 24 to be carried between exercise monitoring units and plugged into any exercise monitoring main unit. When the personal module 24 is inserted into a main unit, the address data bus 144 of the microcomputer 122 is connected to the address latch 42 and to the data bus connectors $O_0$–$O_7$ of EEPROM 44 through the connector 40. The control bus 50 connects the control lines from connector 40 to the control ports for the EEPROM 44* and the address latch 42. The EEPROM 44 upon being addressed, reads data out via the data ports $O_0$–$O_7$ and transmits it to the microcomputer 122. The electrically erasable programmable read only memory (EEPROM) 44 is a nonvolatile memory and can be erased only upon an appropriate electrical signal from the microcomputer 122. In this manner, the data stored in the memory 44 can not be erased unless the personal module is connected to the exercise monitoring main unit 100. Thus the data for the user remains intact while the user transports the personal module or leaves it on site.

3. The Exercise Monitoring Screen.

Figure 4:
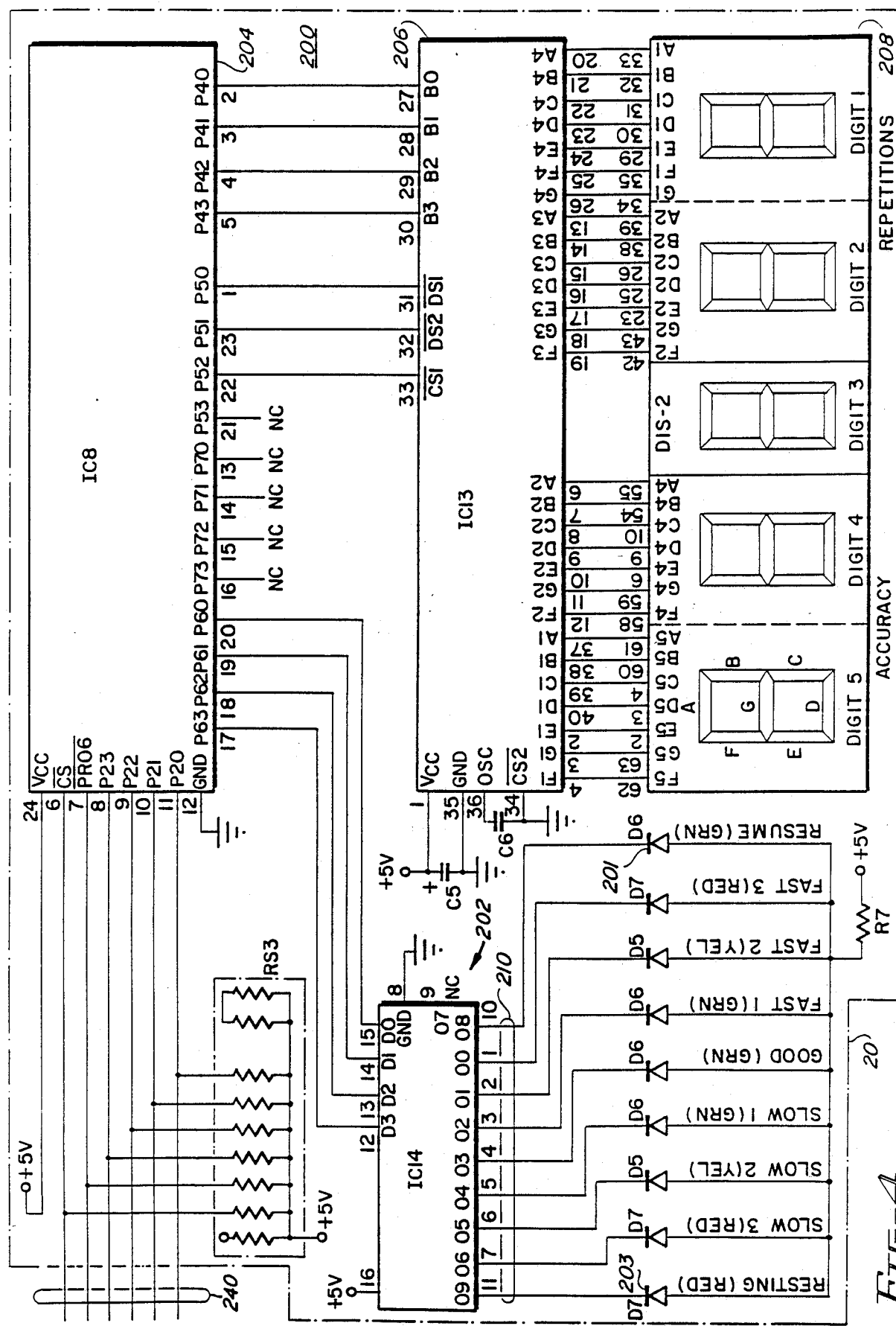
FIG. 4 illustrates a detailed block diagram for the exercise monitoring screen.

Referring to FIG. 4 there is shown a detailed electrical circuit of the exercise monitoring screen. An I/O expander 204 connects the I/O bus 140 to the microcomputer 122. In a manner as described before in the previous I/O expander, the I/O expander 204 communicates through four different I/O ports comprised of four I/O lines each. Ports P60 through P63 are connected to a four by ten decoder 202. The four by ten decoder ICI4 decodes the four ports into 9 output lines 210. The 9 output lines 210 of the decoder are connected to a corresponding LED in the LED display 202. The LED display 202 comprises a row of LEDs for displaying the user's exercise rate performance. The microcomputer 122 controls the illumination of each LED via the I/O expander 204 and the four by ten decoder 202. The illumination of an LED is controlled by the microcomputer 122 software. If the user is performing the exercise routine at a rate equal to the previous exercise routine stored on the personal module 24, the green LEDs are illuminated. A red LED which signifies the user is performing too slow, through a yellow LED to a series of green LEDs, yellow LEDs, and red LEDs. The last red LED activates when the user exercises too fast. If the rate is slow the yellow LED is lit. If the rate is fast the yellow LED on the opposite side is lit. In this manner, the user compares his present performance with his previous performance. The display 202 also has a resume LED 201 and a resting LED 203. The resting LED 203 illuminates when the user rests too long between repetitions. The resume LED 201 illuminates at the height of the repetition after the user pauses.

The I/O expander 204 is also connected to a liquid crystal display controller 206 which is illustratively shown as an ICM7211AMIPL as manufactured by INTERSIL Corporation. The LCD controller 206 controls the liquid crystal display 208, which displays the accuracy numbers and the repetition rate of the user on the exercise machine.

4. The Exercise Monitoring Analyzer.

Referring to FIG. 5 there is shown an electrical diagram of the exercise monitoring analyzer 300. The exercise monitoring analyzer 300 comprises a microprocessor 302 such as that made by IBM and designated as an IBM PC; a personal module connector 310, a keyboard 320, and a I/O connector 316. The personal module 24 physically and electrically connects to the exercise monitoring analyzer 300 through connector 310. The microprocessor 302 receives and transmits data by its address data bus 314 and control bus 312 to the memory personal module 24. The microcomputer 302 reads the data from the personal module 24, and through instructions and data in its program memory 306, computes charts and graphs. They are displayed on the printer/plotter 18 through I/O connector 316. In addition to the output on a printer/plotter 18, a keyboard 318 is available for the user to insert instructions and data into the microprocessor 302. The exercise monitoring analyzer software computes performance characteristics desired by the user from the data.

5. The Exercise Monitoring Sensor.

Referring to FIGS. 6A–E, there are shown the elements and a detailed electrical circuit that comprise the exercise monitoring sensors 20 and 22. Referring to FIG. 6A, the sensor 20 comprises an infrared emitter 56 and an infrared detector 54. Sensor 22 comprises an infrared emitter 50 and detector 52. The sensor 20 and 22 are connected to the microcomputer 122 through bus 143. The bus 143 includes output lines 124 and 126, and power lines to operate the sensors. A TTL level output signal generates from the detector when infrared light from a emitter strikes it.

Referring now to FIG. 6B there is shown a construction of the sensors to measure the rotation of a disc 38 having a plurality of equally spaced holes 40 along the perimeter. The sensors are mounted so that when an opening passes between an emitter and detector, infrared light from the emitter strikes the surface of the detector. Referring to FIG. 6C, the plastic or metal disc 38 is fixed onto the reel 58 mounted on base 64. A metal ring 28 is connected by a screw or other method to the chain of a weight stack or other moving part of the exercise machine. As the cable 26 is pulled off the reel 58 the attached disc 38 rotates clockwise with the eight openings 40 interrupting the infrared beams of emitters 56 and 50 such that the outputs of the infrared detectors 52 and 54 oscillate as shown in FIG. 6D. A built in spring in the base mounted reel 58 winds the cable 62 back onto the reel 58 causing disc 38 to rotate counterclockwise. The sensors 20 and 22 are mounted so that a clockwise rotation of 38 creates two waveforms 90 degrees out of phase between sensor 20 and 22. The counterclockwise rotation creates two waveforms 270 degrees out of phase. The exercise monitoring main unit continuously monitors output of the sensors 20 and 24 to keep track of the position of the moving weight stack. A clockwise rotation creates a sequence of TTL outputs like 10 11 01 00 10 11 01 00 10                State (1)

A counterclockwise rotation creates a sequence of outputs such as 01 11 10 00 01 11 10 00 01               State (2)

When the sequence of TTL outputs go to zero (00) in the clockwise rotation, the exercise monitoring main unit increments a position counter to signify that the weight stack has moved in a particular direction, a corresponding counterclockwise rotation decrements the position counter when the sequence of outputs go to zeros (00). In this manner, the exercise monitoring main unit continuously monitors the movement of the weight stack and can measure the rate of the weight stack and its exact location.

Referring to FIG. 6E, there is shown another embodiment of the sensor operation for directly measuring the movement of a chain 66 connected to a weight stack. The chain 66 includes links separated by a distance X. The sensors 20 and 22 are contained in a sensor block 68. The sensor block is connected to the frame of the exercise machine. The sensor block 68 receives the chain 66 into slot 70 in such a manner that the chain 66 can move freely through the sensor block 68. When the chain 66 moves, the links interrupt the light between the emitters and detectors of sensors 20 and 22. The distance Y is calculated to produce two waveforms 90° out of phase between sensors 20 and 22, when chain 66, with links separated by distance X, moves perpendicular to the line of sight of sensors 20 and 22. The sensors thus produce an output as described before when the chain moves. In this manner, the sensors detect the movements of the chain.

6. Flow Chart of Exercise Monitoring System.

Referring now to FIG. 7, there is shown a high level flow diagram of the method in which the exercise monitoring system of this invention operates to record and measure the exercising data in a form that intelligibly informs the user of his exercising progress. Initially in step 350 the user presses the start button on the exercise monitoring main unit. Thereafter in step 351, initialization routines are performed to begin the operation of the exercise monitoring main unit. Subsequently in step 352, the changed position as measured by the exercise monitoring sensors is measured. The software then continues to step 354, in which the membrane switch pad is monitored to determine whether any switch is pressed. If a switch is pressed, a service request of action is made operational depending upon which action is requested.

The service requested action results from the pressing of the date button, the learn switch, the review switch, or the decrementing or incrementing of a seat selection, or the decrementing or incrementing of a weight selection. The changing of the seat selection corresponds to the seat position on the exercise machine. The weight selection corresponds to the number of weights selected by the user in his exercising routine. For example, if the user is selecting three weights the user will input into the exercise monitoring unit the letter C which corresponds to three weights. Similarly, a seat selection will have a corresponding letter to signify the position of the seat.

As shown is step 354, if no switch is hit or if a service requested action is completed, the routine continues to step 358, in which the exercise monitoring screen is updated. The exercise monitoring screen displays the accuracy number and the rate in which the exercise repetition is being completed. The accuracy number, which appears on the exercise monitoring screen, represents how closely the user's repetition matches the personal best efforts or previous effort of the user, as has been stored in the personal module. If a completed repetition nearly duplicates the best efforts the accuracy number is 99 which signifies that the best personal effort of the user is within 99 percent of duplication. The factors which lower the accuracy number are exercising too fast or too slow, resting, and not pausing at the height of the repetition. In addition to the accuracy number display, a repetition count is displayed. The repetition count is incremented by one when the distance traveled by the weight is 87.5% of that distance recorded in the user's previous effort.

In addition to displaying an accuracy number and repetition number the exercising monitoring screen also has a horizontal row of red, yellow and green to indicate the rate of exercise. While the user exercises a red light on the exercise monitoring screen turns on when the member rests in between repetitions to discourage resting, and a green light turns on at the height of each repetition to encourage the user to pause momentarily. The row of red, yellow and green lights indicate whether the user is exercising too slow, too fast, or just right. The routine then continues to step 360 in which the exercise monitoring main unit determines if a repetition has been completed. If not, the exercise monitoring main unit updates the chain position and repeats the procedure beginning with step 352. If the user has completed a repetition the routine continues to step 362. In step 362, the exercise monitoring unit calculates the accuracy number as has been described before and displays the accuracy number for the user. After the accuracy number has been displayed, the system is initialized for the next repetition in step 364. The procedure then begins again as step 352.

7. Detail Flow Diagram of the Learn Routine.

Figure 8A:
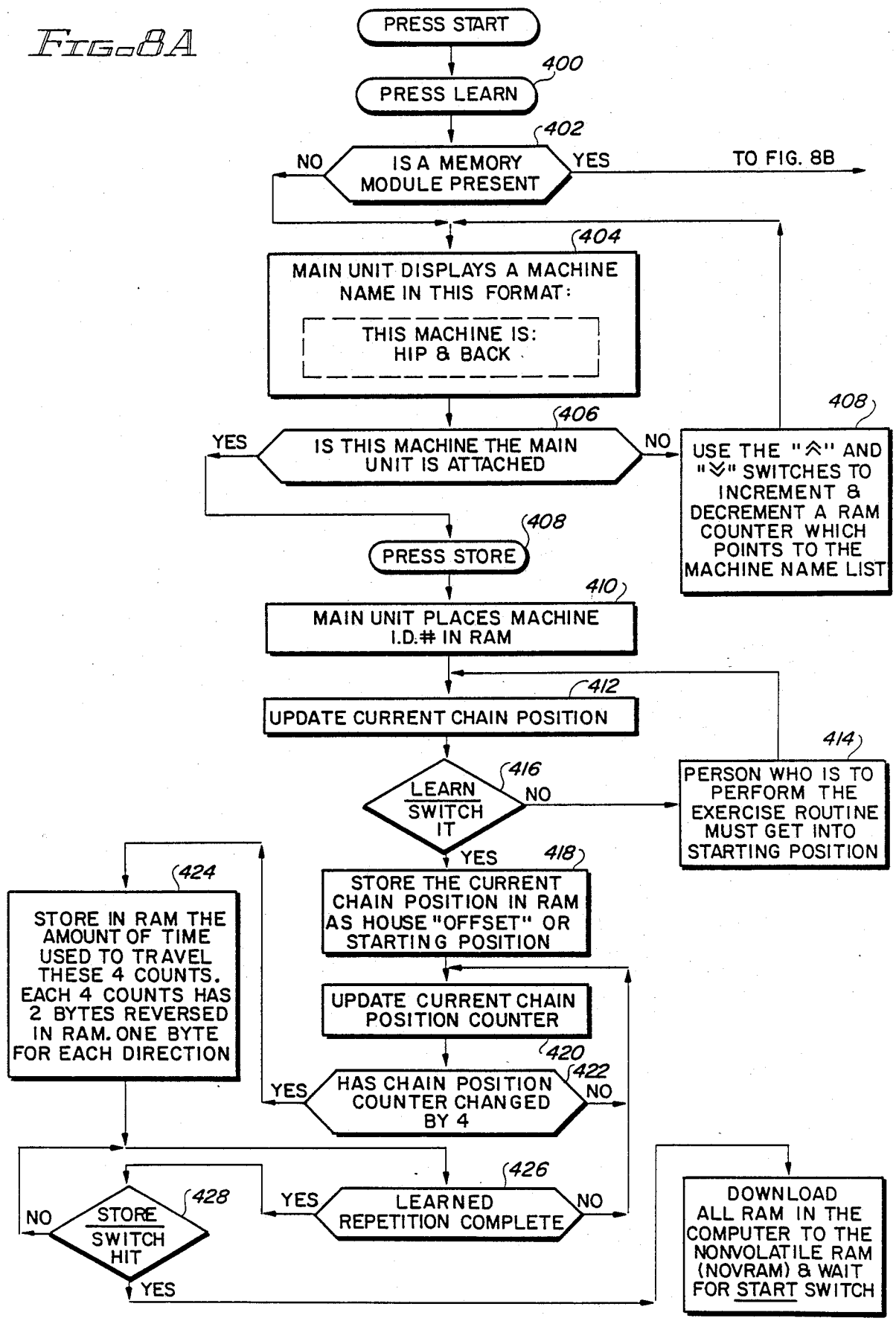
FIGS. 8A-B show a detailed flow diagram of the learned routine for the exercise monitoring main unit.
Figure 8B:
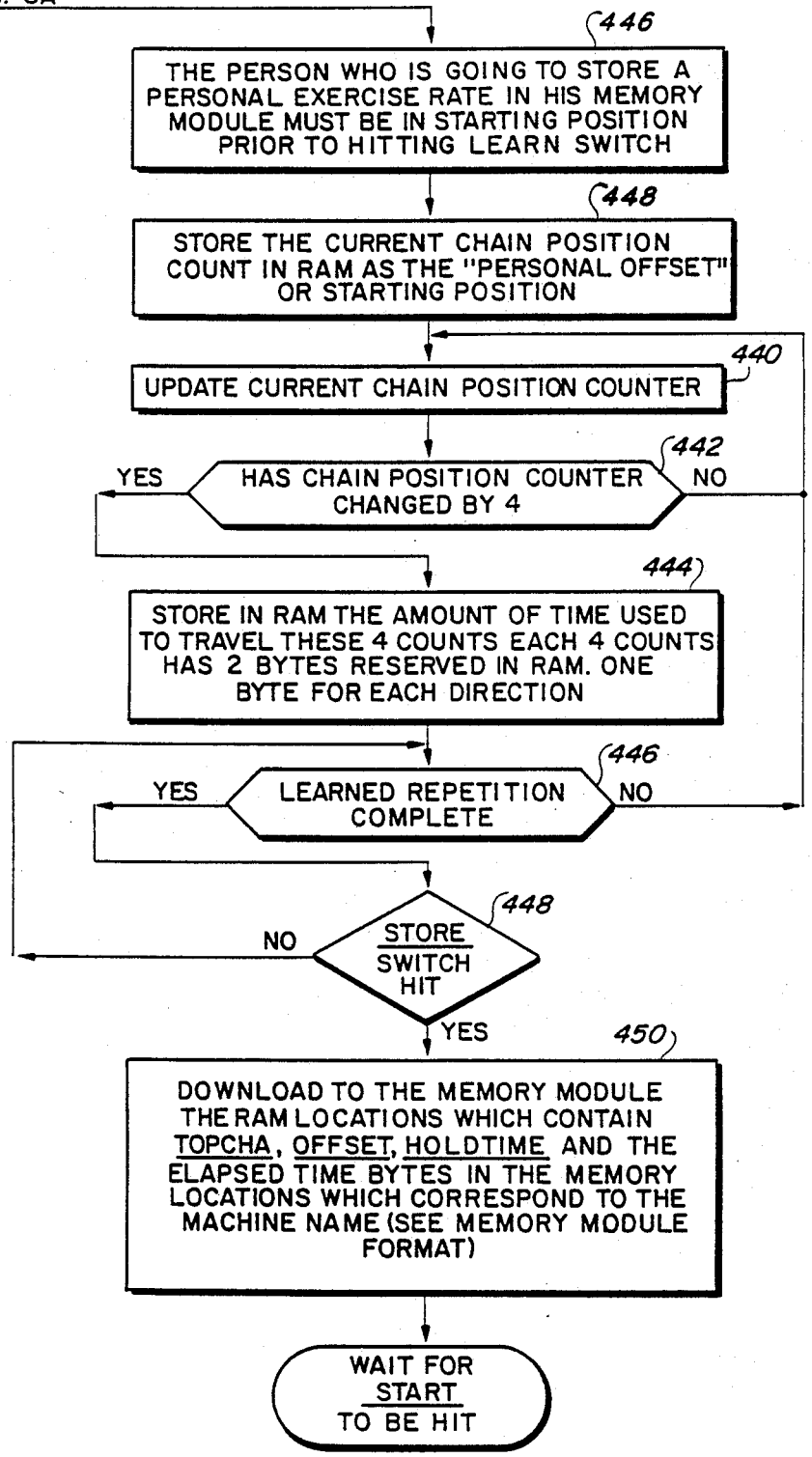

Referring to FIGS. 8A-B, there are shown a detailed flow chart of the exercise monitoring main unit software that is implemented on the pressing of the learn switch on the exercise monitoring switchpad. The learn switch is used for storing the exercise routine into the personal module or NOVRAM, if a personal module is not present. Upon pressing the learn switch, in step 400, the software determines if a personal module is present in step 402. If the personal module 24, is not present the exercise monitoring main unit displays a machine name on the exercise monitoring main unit LCD display, as shown in step 404. If this is the machine that the exercise monitoring main unit is attached, the user stores the machine identification as shown in steps 406, 408 and 410. If the exercise monitoring main unit is not attached to the exercise machine shown in the LCD display of the main unit, the operator uses the increment and decrement switches to increment and decrement a RAM counter, which points to the machine name list as shown in 408. The routine then begins agains at step 404 in which the exercise monitoring main unit displays the new machine name in the format. When the correct exercise machine is displayed in the LCD display, the user then presses store as shown in step 408. The exercise monitoring main unit then places the machine ID into the RAM as shown in step 410. The routine then continues at step 412, in which the current chain position is updated. The software then waits for the learn switch to be hit again before continuing.

Before the learn is pressed, the person who is to perform the exercise routine must get into the starting position, as shown in step 414. When the person is in the starting position, the routine then begins again at 412 to update the current chain position. When the learn switch is hit as shown in step 416, the exercise monitoring operating software stores the current chain position in the RAM as an offset starting position as shown in step 418. The software, then continues to step 420, in which the current chain position counter is updated. If the current chain position counter has changed by four as shown in step 422, the amount of time used to travel through four counts is computed, as shown in step 424. In this manner, the rate of exercise is determined for the user. If the chain position is not changed by four, the current chain position counter is read until the change by four is accomplished. In step 424, the amount of time used to travel these four counts is stored. The procedure then continues to step 426, to determine whether the learn repetition is complete. If the learned repetition is not complete, the update current chain position is again monitored as previously described. If the repetition is complete, the procedure continues to step 428, where it waits until the user presses the store switch. If the user does not press the store switch, the system continues the learn repetition, cycle as step 426. When the store switch is hit, step 428, the data in the internal RAM of the microcomputer 122, is down loaded to the NOVRAM and waits for the start switch. In this manner, a coach or a standard performance is stored in the NOVRAM so that a user can compare his exercising routine to the coach's or another person's performance.

Referring back to step 400, if the learn switch is pressed and a personal module is present the system begins operation at step 403 as shown in FIG. 8B. This signifies that the user is going to store into the personal module an exercise performance rate in which he will later compare his future exercising routine. The current chain position in the RAM is stored as the personal offset or starting position as shown in step 405. The routine then continues in step 440, in which the current chain position counter is updated, if the current chain counter is changed by four as shown by step 442, the system goes to step 444, in which the amount of time used to travel four counts is recorded. If the current chain position counter is not changed by four the routine, cycles back to step 440 to update the current chain position again. After the time to travel the four counts has been determined, the repetition cycle continues again at step 440, as shown in step 446. In this manner, the chain position is constantly monitored as the user exercises and his rate of exercise is stored in the RAM of the exercise monitoring main unit. Upon completion of the learn repetition cycle the store switch is pressed as shown in step 448. When the store switch is pressed, the internal RAM data of the microcomputer 122 is down loaded to the personal module 24. In this method, the efforts of the user for this particular repetition are stored in the personal module for comparison to future performance of the user's repetitions.

8. Detailed Flow Diagram of the Date Routine.

Figure 9:
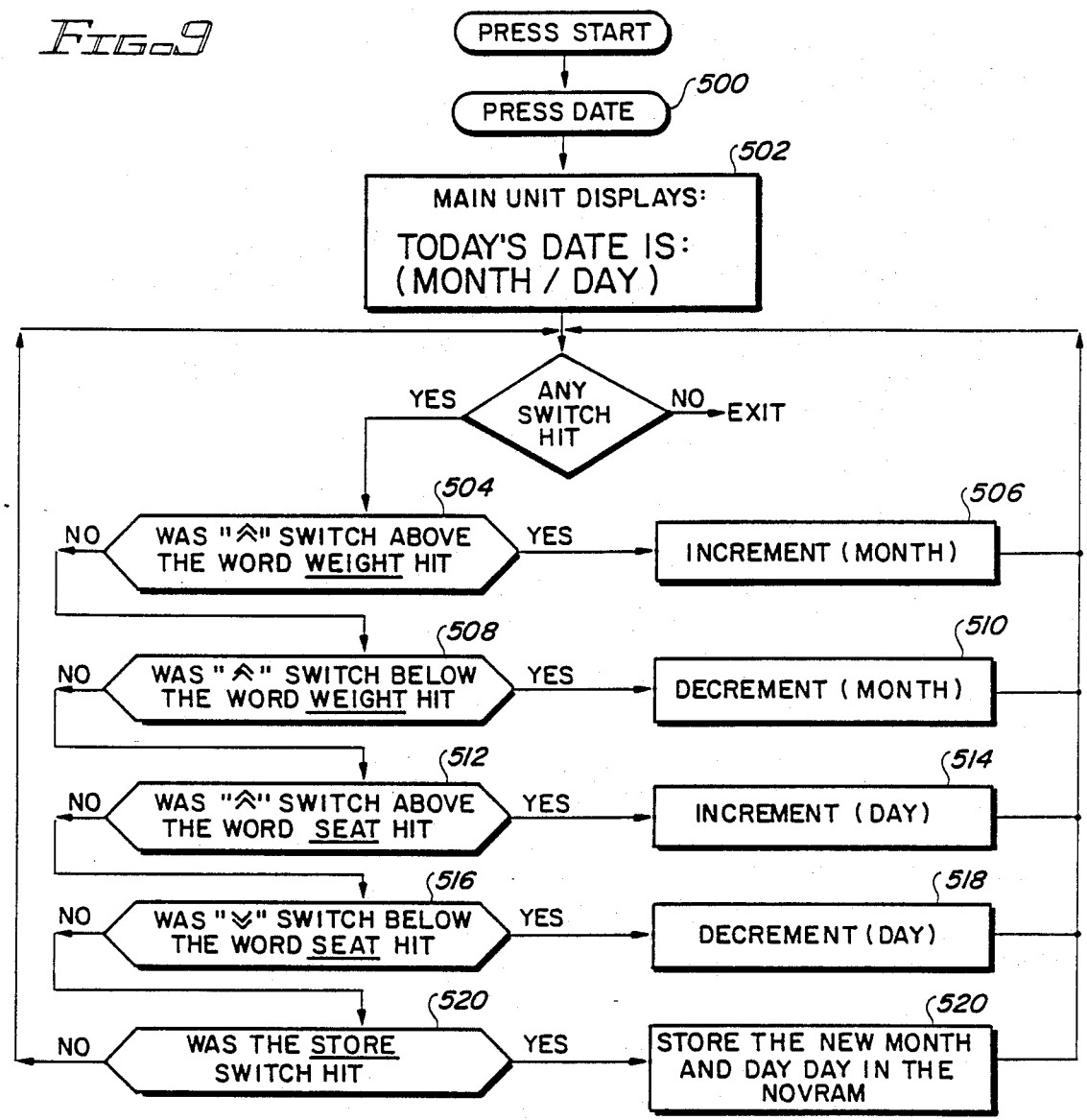
FIG. 9 illustrates a detailed flow diagram of the date routine for the exercise monitoring main unit.

Referring to FIG. 9 there is shown the detailed diagram of the date routine. Upon the pressing of the date switch as shown in step 500, the exercise monitoring main unit displays the date as month/day as shown in step 502. If a first increment switch stationed above the word "weight" is pressed the month is incremented as shown in steps 504 and 506. If a first decrement switch below the work "weight" is pressed the month is decremented as shown in steps 508 and 510. If a second increment switch above the word "seat" is pressed, the day is incremented as shown in steps 512 and 514. If a second decrement switch below the word "seat" is pressed, the day is decremented as shown in steps 516 and 518. At the completion, if the store switch is hit as shown in step 520, the new month and day are stored in the NAVROM as shown in step 522.

9. Detailed Flow Diagram of the Review Routine.

Figure 10:
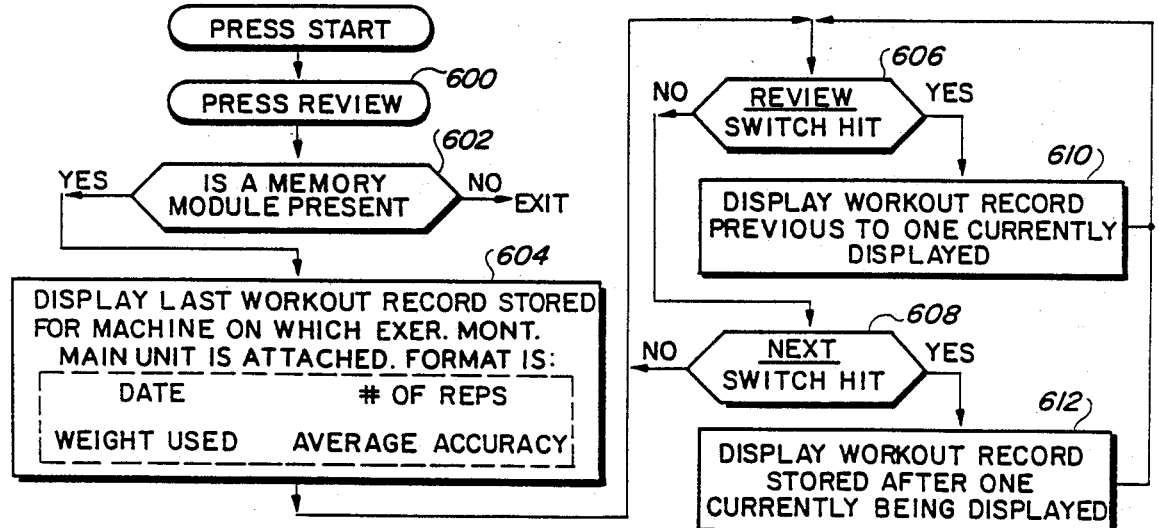
FIG. 10 shows a flow diagram for the review routine for the exercise monitoring main unit.

Referring now to FIG. 10 there is shown the detailed flow diagram of the review routine. Beginning in step 600 the review switch is pressed. The exercise monitoring main unit then determines if a personal module is present, as shown in step 602. If one is not present the routine exits; if one is present the routine continues to step 604. In step 604, the last workout record stored for the machine on which the exercise monitoring main unit is attached is displayed. The display is in the form of date, number of repetitions, weight used and average accuracy. If the review switch is pressed again, as shown in step 606, the workout record previous to the current one is displayed, step 610. If instead of the review switch being pressed in step 606, the next switch is pressed, as shown is step 608, the display workout record stored after the one currently being displayed is shown, step 612. The routine continues displaying workout records until the start switch is pressed again.

10. Initialize Routines.

Referring now to FIG. 11 there is shown a detail flow diagram of the initialize routines. Beginning in step 700, the internal RAM of the main unit is cleared and the exercise monitoring screen display is blanked out. The exercise parameters from the particular exercise machine are recalled from the NOVRAM and placed into the internal RAM of the microcomputer of the exercise monitoring main unit as shown in step 702. The routine continues at step 704, where it is determined if a personal module is present. If a personal module is present, the personal exercise parameters from the personal module are recalled and they are place in the internal RAM of the microcomputer of the exercise monitoring main unit, as shown in step 706. The weight and seat settings last used on this exercise machine for this particular user are displayed on the exercise monitoring main units display. If a personal module is not present, as shown in step 704 the display shows a standard exercise name on the display unit on the main unit, as shown in step 710. This concludes the end of the initialize routine.

11. Routine To Update The Chain Position.

Figure 12:
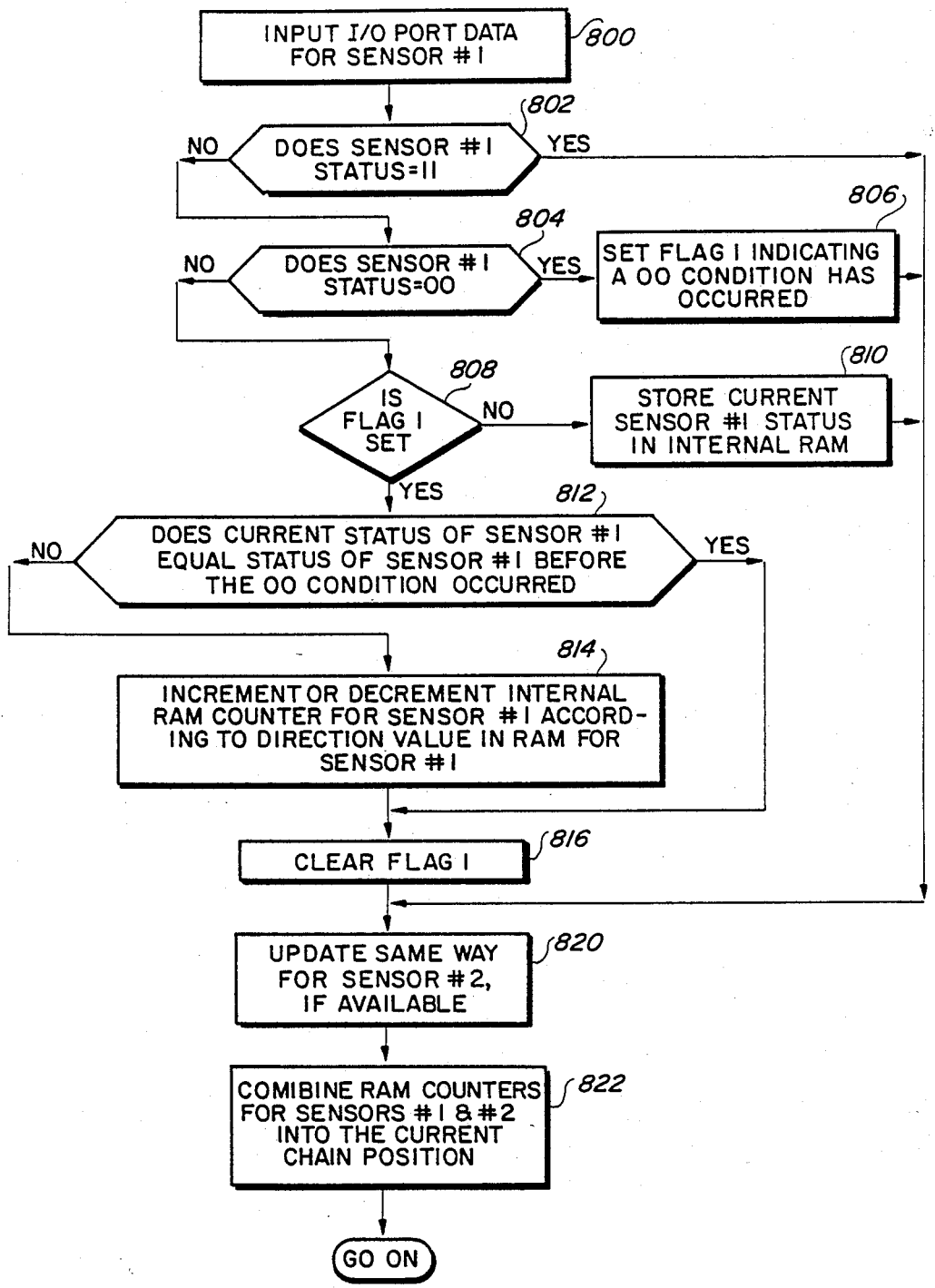
FIG. 12 shows a flow diagram for the update of the chain position routine for the exercise monitoring main unit.

Referring now to FIG. 12, there is shown a detailed flow diagram to update the chain position. The chain position is updated by sampling a pair of sensors. For some exercise machines an additional pair of sensors are required. The software is written to accomodate a second pair of sensors, if they are required. Sampling of the first pair of sensors is accomplished by sampling each detector lines. If the first detector line is high this results in a "1", and if low, a result of "0" is obtained. The second detector is sampled in the same manner. When each detector line is sampled, it results in a state of 00, 01, 10, or 11. Since the sensors are 90° out of phase, a 00 can not follow a 11, only a 01 or a 10 can begin or follow a 00. The routine looks for a 00 to either increment or decrement the counter for the pair of sensors. The software thus checks the before and after state of the 00 transition state to determine whether to increment or decrement the counter. It is important to note, that the routine goes through and samples each sensor only once and then exits. The software of the microcomputer is very much faster than the slow moving chain, so that when the software samples the sensors again, the microcomputer has not missed any transition states.

In step 800, the microcomputer for the exercise monitoring main unit inputs the data for the first pair of sensors, which in this particular embodiment are sensors 20 and 22. The microcomputer then determines the status of the sensors to see whether the status of the sensors is equal to a 11 transition, as shown in step 802. The microcomputer is looking for a sequence of TTL outputs from each pair of sensors of 01 00 10, which is an increment, or 10 00 01, which is a decrement. An increment or decrement signifies the chain has moved a known distance in a known direction, and thus the movement in the weight stack can be calculated. A transition of 11 never occurs before a 00 state, and therefore sensors reading of 11 mean that the next number is not a 00, so the input from the sensors is skipped, and the input from the second pair of sensors is read. If the sensor status is 11 the routine continues to 820, to update the second pair of sensors. If the first pair of sensors do not have a status of 11 the routine continues to step 804. This means that the transition will be at 01, 10 or 00.

In step 804, the microcomputer determines if the status of the sensors is 00. If the status of the sensors is 00, a flag is set indicating that a 00 condition has occurred on the first pair of sensor as shown in step 806 and the routine then continues to step 820. If the first pair of sensors do not have the status of 00, the routine continues to step 808. In step 808, the first flag is checked to see if it has been set or not. If the flag is not set, meaning no 00 condition has occurred, the current status of the first sensors is stored in the internal RAM as shown in step 810 and the routine continues to step 820. Note that the current status of the sensors will be either a 10 or 01, at step 810.

If the first flag is set as shown in step 808, the routine continues to step 812. This signifies that the sensors have gone through a 00 state. In step 812, the current status of the first pair of sensors is checked with the status of the first pair of sensors before the 00 condition occurred. If the current status does equal the current status of the first pair of sensors before the 00 condition occurred, the chain has not really moved but "bounced". Therefore, the sensor's counter is not incremented or decremented. The first flag is cleared as shown in step 816 and the same procedure is repeated for the second sensor, as shown in step 820. In step 814, if the current status of the first pair of sensors is not equal to the current status of the first pair of sensor before the 00 condition occurred, the internal RAM counter is incremented or decremented for the first pair of sensors according to the direction from the store transition state saved in step 810. This signifies that the sensor has made a transition of 01 00 10 and the counter incremented or the sensor has made a transition of 10 00 10 in which case the counter is decremented. The first flag is then cleared as shown in step 816. The routine then continues to step 820.

In step 820, if a second pair of sensors are available, the second pair of sensors are updated in the same way as the first pair of sensors. The routine is the same, and is not repeated here for brevity. The routine then continues to step 822, in which the combined RAM counters for the first pair of sensors and the second pair of sensors are combined into the current chain position. The counters are added together and then divided by two to get an average. From this average count the current chain position is quickly, easily and accurately determined.

12. Exercise Monitoring Analyzer Software.

The exercise monitoring analyzer software reads the data from the personal module and computes charts and graphs, depending upon the particular inputs of the user. The exercise monitoring analyzer is provided to give the user a graphic description of his exercise progress on a particular machine or on a series or machines. The data is displayed in a convenient form on a printer/plotter unit 18. The exercise monitoring analyzer programs may be written in a machine language, or at a higher language using procedures appropriate for the actual microprocessor in use, to execute the required computations herebefore described. A suitable computer for the exercise monitoring analyzer is a general purpose microprocessor, such as an IBM PC. Alternatively, one or more microprocessors similar to the IBM PC may be suitably interconnected and programmed to perform the functions required of the exercise monitoring analyzer. The programs on the exercise monitoring analyzer compute the user's performance and faults, and provide a result of the user's performance in a form more suitable for analysis, such as tables and graphs.

In summary, the present invention provides a system for monitoring a user's present performance on an exercise machine, and compares his past performance to the user's present performance on that particular machine. The user's past performance is stored on a portable personal module memory unit which is transferred from one exercise machine to another. The invention provides the user with the ability to compare his performance on any exercise machine with his previous best personal effort for that particular machine.

Thus, although the best mode for carrying out the present invention have been herein shown and described, it will be apparent that modification and variation may be made without departing from what is regarded as the subject matter in the invention.

We claim:

1. A system for monitoring a user's exercise performance on an exercise machine, said system comprising:
monitoring means for monitoring a user's current exercise activity on the exercise machine and for providing monitor signals representative thereof;
memory means for storing data representative of exercise activity different from said current exercise activity on the exercise machine and for producing output signals representative thereof;
evaluating means operably coupled with said monitoring means and said memory means for receiving and evaluating said monitor signals and said output signals respectively and in response thereto for producing display signals representative of an evaluation of said monitor signals and said output signals with respect to one another;

display means for receiving said display signals and, in response thereto, for producing a display representative of said evaluation, said evaluation being thereby representative of said current exercise activity with respect to said different exercise activity;

said memory means further comprising a portable, replaceable memory module detachable from said system; and means allowing replacement of said module by a different memory module associated with another user.

2. The system as set forth in claim 1, said different exercise activity including exercise activity of the user occuring prior to said current exercise activity.

3. The system as set forth in claim 2, said memory means being operable for storing data representative of said current exercise activity for evaluation with respect to some future exercise activity on the exercise machine.

4. A system for monitoring a user's exercise performance on an exercise machine, said system comprising:

monitoring means for monitoring a user's current exercise activity on the exercise machine and for providing monitor signals representative thereof;

memory means for storing data representative of exercise activity different from said current exercise activity on the exercise machine and for producing output signals representative thereof;

evaluating means operably coupled with said monitoring means and said memory means for receiving and evaluating said monitor signals and said output signals respectively and in response thereto for producing display signals representative of an evaluation of said monitor signals and said output signals with respect to one another; and display means for receiving said display signals and, in response thereto, for producing a display representative of said evaluation, said evaluation being thereby representative of said current exercise activity with respect to said different exercise activity;

said evaluation being a percentage representative of said current exercise activity compared to said different exercise activity.

5. A method of monitoring a user's exercise performance on an exercise machine comprising the steps of:

monitoring the user's current exercise activity on the exercise machine and providing monitoring signals representative thereof;

providing memory means having data stored therein representative of exercise activity different from said current activity on the exercise machine and providing memory signals representative of said different exercise activity;

evaluating said monitoring signals and said memory signals in order to produce an evaluation of said current exercise activity with respect to said different exercise activity;

producing a digital numerical display representative of said evaluation; and providing said memory means a replaceable, portable memory module replaceable by another memory module associated with another user.

6. The method as set forth in claim 5, further including the step of storing data representative of said current exercise activity in said memory means.

7. The method as set forth in claim 5, said evaluating step including the step of providing said evaluation as a percentage comparison of said current exercise activity with respect to said other exercise activity.

8. The method as set forth in claim 5, said display including a numerical digital display.

* * * * *